(12) United States Patent
Kim et al.

(10) Patent No.: US 9,689,043 B2
(45) Date of Patent: Jun. 27, 2017

(54) METHOD FOR TREATING MUSCLE-INVASIVE BLADDER CANCER, CONTAINING S100A9 AND EGFR INHIBITORS AND CISPLATIN AS ACTIVE INGREDIENTS

(71) Applicant: CHUNGBUK NATIONAL UNIVERSITY INDUSTRY—ACADEMIC COOPERATION FOUNDATION, Cheongju-si (KR)

(72) Inventors: Wun-Jae Kim, Cheongju-si (KR); Seok-Joong Yun, Cheonju-si (KR); Won-Tae Kim, Cheongju-si (KR)

(73) Assignee: Chungbuk National University Industry-Academic Cooperation Foundation, Cheongju-si (KR)

( * ) Notice: Subject to any disclaimer, the term of this patent is extended or adjusted under 35 U.S.C. 154(b) by 0 days.

(21) Appl. No.: 14/744,468

(22) Filed: Jun. 19, 2015

(65) Prior Publication Data

US 2016/0017432 A1    Jan. 21, 2016

Related U.S. Application Data

(63) Continuation-in-part of application No. PCT/KR2013/008775, filed on Oct. 1, 2013.

(30) Foreign Application Priority Data

Dec. 20, 2012    (KR) ........................ 10-2012-0149641

(51) Int. Cl.
| | |
|---|---|
| *C12Q 1/68* | (2006.01) |
| *G01N 33/574* | (2006.01) |
| *C12N 15/113* | (2010.01) |
| *A61K 39/395* | (2006.01) |

(52) U.S. Cl.
CPC .......... *C12Q 1/6886* (2013.01); *C12N 15/113* (2013.01); *G01N 33/57407* (2013.01); *A61K 39/39533* (2013.01); *C12N 2310/14* (2013.01); *C12N 2320/31* (2013.01); *C12Q 2600/106* (2013.01); *C12Q 2600/112* (2013.01); *C12Q 2600/118* (2013.01); *C12Q 2600/158* (2013.01); *G01N 2333/4727* (2013.01); *G01N 2333/71* (2013.01); *G01N 2800/52* (2013.01)

(58) Field of Classification Search
None
See application file for complete search history.

(56) References Cited

U.S. PATENT DOCUMENTS

2011/0059459 A1    3/2011 Roca et al.

OTHER PUBLICATIONS

Shrader, M. et al., "Molecular correlates of gefitinib responsiveness in human bladder cancer cells" Mol Cancer Ther 2007;6(1). Jan. 2007.*
Phillips et al., A phase II trial of cisplatin (C), gemcitabine (G) and gefitinib for advanced urothelial tract carcinoma: results of Cancer and Leukemia Group B (CALGB) 90102, Annals of Oncology 20: 1074-1079, 2009.*
Kim, Wun-Jae et al., A Four-Gene Signature Predicts Disease Progression in Muscle Invasive Bladder Cancer, Mol Med 17(5-6):478-485, (2011).
Kim, Wun-Jae et al., A Four-Gene Signature Predicts Disease Progression in Muscle Invasive Bladder Cancer, Mol Med 17 (5-6):478-485, (2011).
Yao, Ruisheng et al., "Expression of S100 Protein Family Members in the Pathogenesis of Bladder Tumors," Anticancer Research 27: 3051-3058 (2007).
Blaveri, Ekaterini, et al., "Bladder Cancer Outcome and Subtype Classification by Gene Expression," Clin Cancer Res, 11:4044-4055 (2005).
Kim, Wun-Jae, et al., Predictive value of progression-related gene classifier in primary non-muscle invasive bladder cancer, Molecular Cancer 9(3):1-9, (2010).
Kim, Wun-Jae, et al., "S100A9 and EGFR gene signatures predict disease progression in bladder cancer patients after chemotherapy," Fukuoaka SIU, 2012.
Kim, Wun-Jae, et al., "Gene Signature of S100A9 and EGFR as Factor to Predict Anticancer Treatment Response in Bladder Cancer Patient Undergone Anticancer Treatment," Korean Journal of Urology, 53(2):49, (2012), English Abstract.

* cited by examiner

*Primary Examiner* — Lorraine Spector
(74) *Attorney, Agent, or Firm* — Joseph Hyosuk Kim; JHK Law

(57) ABSTRACT

The present invention relates to a method for predicting the probability of muscle-invasive bladder cancer (MIBC) recurrence or metastasis, a method for providing information on a personalized medicine of MIBC, and a pharmaceutical composition for treating MIBC, containing S100A9 and EGFR inhibitors and cisplatin as active ingredients. According to the present invention, it is possible to accurately predict a prognosis after chemotherapy of an MIBC patient, to provide information on cisplatin sensitivity in the provision of a personalized medicine for chemotherapy of an MIBC patient, and to increase the cisplatin sensitivity of an MIBC patient by concomitantly administering S100A9 and EGFR inhibitors together with a conventional cisplatin.

1 Claim, 12 Drawing Sheets

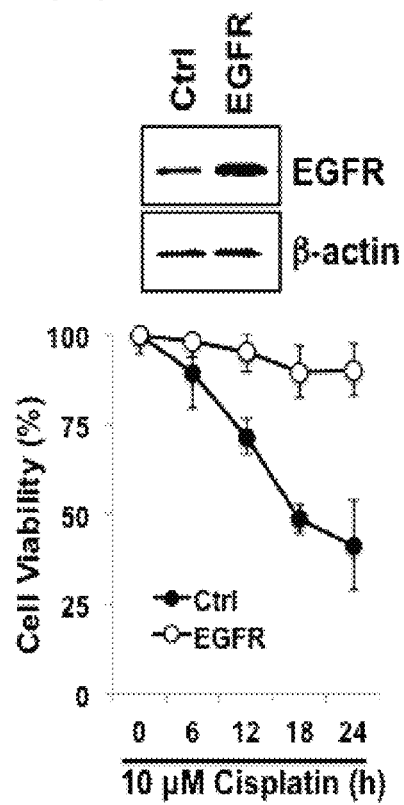
FIG. 5A
FIG. 5B
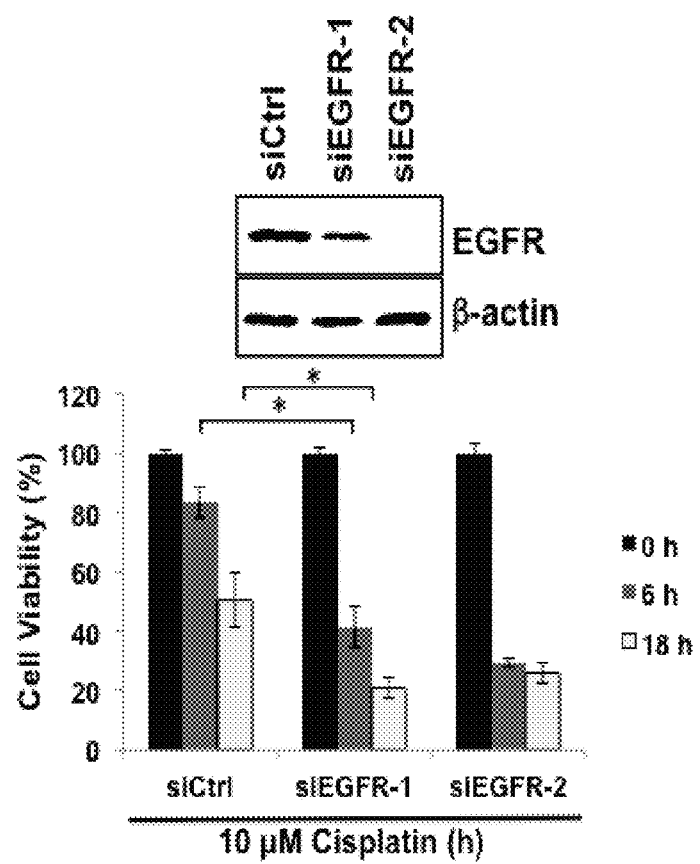
FIG. 5C
FIG. 5D

SEQUENCE LISTING

```
<160> NUMBER OF SEQ ID NOS: 12

<210> SEQ ID NO 1
<211> LENGTH: 345
<212> TYPE: DNA
<213> ORGANISM: Artificial Sequence
<220> FEATURE:
<223> OTHER INFORMATION: S100A9 cDNA seq.

<400> SEQUENCE: 1
atgacttgca aaatgtcgca gctggaacgc aacatagaga ccatcatcaa caccttccac      60
caatactctg tgaagctggg gcacccagac accctgaacc aggggggaatt caaagagctg     120 gtgcgaaaag atctgcaaaa tttctcaag aaggagaata agaatgaaaa ggtcatagaa        180
cacatcatgg aggacctgga cacaaatgca gacaagcagc tgagcttcga ggagttcatc      240
atgctgatgg cgaggctaac ctgggcctcc cacgagaaga tgcacgaggg tgacgagggc      300
cctggccacc accataagcc aggcctcggg gagggcaccc cctaa                      345

<210> SEQ ID NO 2
<211> LENGTH: 114
<212> TYPE: PRT
<213> ORGANISM: Artificial Sequence
<220> FEATURE:
<223> OTHER INFORMATION: S100A9 aminoacid seq.

<400> SEQUENCE: 2

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
```

```
                    35                  40                  45
Leu Lys Lys Glu Asn Lys Asn Glu Lys Val Ile Glu His Ile Met Glu
         50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                 85                  90                  95

Gly Asp Glu Gly Pro Gly His His His Lys Pro Gly Leu Gly Glu Gly
            100                 105                 110

Thr Pro

<210> SEQ ID NO 3
<211> LENGTH: 3633
<212> TYPE: DNA
<213> ORGANISM: Artificial Sequence
<220> FEATURE:
<223> OTHER INFORMATION: EGFR cDNA seq.

<400> SEQUENCE: 3
atgcgaccct ccgggacggc cggggcagcg ctcctggcgc tgctggctgc gctctgcccg      60
gcgagtcggg ctctggagga aagaaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaaac cgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg gagctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat tccgagacga agccacgtgc     780
aaggacacct gccccccact catgctctac aaccccacca cgtaccagat ggatgtgaac     840
cccgagggca atacagcttt ggtgccacct gcgtgaaga agtgtcccc gtaattatgtg     900 gtgacagatc acggctcgtg cgtccgagcc tgtggggccg acagctatga gatgggagaa     960
gacggcgtcc gcaagtgtaa gaagtgcgaa gggccttgcc gcaaagtgtg taacggaata    1020
ggtattggtg aatttaaaga ctcactctcc ataaatgcta cgaatattaa acacttcaaa    1080
aactgcacct ccatcagtgg cgatctccac atcctgccgg tggcatttag gggtgactcc    1140
ttcacacata ctcctcctct ggatccacag gaactggata ttctgaaaac cgtaaaggaa    1200
atcacagggt ttttgctgat tcaggcttgg cctgaaaaca ggacggacct ccatgccttt    1260
gagaacctag aaatcataca cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaaactg    1440
tttgggacct ccgtcagaa aaccaaaatt ataagcaaca gaggtgaaaa cagctgcaag    1500
gccacaggcc aggtctgcca tgccttgtgc tcccccgagg ctgctgggg cccggagccc    1560 agggactgcg tctcttgccg gaatgtcagc cgaggcaggg aatgcgtgga caagtgcaac    1620
```

```
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggcccccac tgcgtcaaga cctgcccggc aggagtcatg    1800
ggagaaaaca acaccctggt ctggaagtac gcagacgccg ccatgtgtg ccacctgtgc     1860 catccaaact gcacctacgg atgcactggg ccaggtcttg aaggctgtcc aacgaatggg    1920
cctaagatcc cgtccatcgc cactgggatg gtggggccc tcctcttgct gctggtggtg     1980
gccctgggga tcggcctctt catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga agccaacaa ggaaatcctc     2280 gatgaagcct acgtgatggc cagcgtggac aaccccacg tgtgccgcct gctgggcatc     2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaattt acacagaatc tatacccacc agagtgatgt ctggagctac     2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atgccccgag accccagcg ctaccttgtc     2940 attcagggg atgaaagaat gcatttgcca agtcctacag actccaactt ctaccgtgcc     3000
ctgatggatg aagaagacat ggacgacgtg tggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg gctgcaaag ctgtcccatc     3180 aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac    3420 actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                3633
```

<210> SEQ ID NO 4
<211> LENGTH: 1210
<212> TYPE: PRT
<213> ORGANISM: Artificial Sequence
<220> FEATURE:
<223> OTHER INFORMATION: EGFR aminoacid seq.

<400> SEQUENCE: 4

-continued

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
```

-continued

```
                420             425             430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
            770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
            835                 840                 845
```

-continued

Gln His Val Lys Ile Thr Asp Phe Gly Leu Ala Lys Leu Leu Gly Ala
    850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
                980                 985                 990
Thr Asp Ser Asn Phe Tyr Arg Ala Leu Met Asp Glu Glu Asp Met Asp
            995                 1000                1005
Asp Val Val Asp Ala Asp Glu Tyr Leu Ile Pro Gln Gln Gly Phe
    1010                1015                1020
Phe Ser Ser Pro Ser Thr Ser Arg Thr Pro Leu Leu Ser Ser Leu
    1025                1030                1035
Ser Ala Thr Ser Asn Asn Ser Thr Val Ala Cys Ile Asp Arg Asn
    1040                1045                1050
Gly Leu Gln Ser Cys Pro Ile Lys Glu Asp Ser Phe Leu Gln Arg
    1055                1060                1065
Tyr Ser Ser Asp Pro Thr Gly Ala Leu Thr Glu Asp Ser Ile Asp
    1070                1075                1080
Asp Thr Phe Leu Pro Val Pro Glu Tyr Ile Asn Gln Ser Val Pro
    1085                1090                1095
Lys Arg Pro Ala Gly Ser Val Gln Asn Pro Val Tyr His Asn Gln
    1100                1105                1110
Pro Leu Asn Pro Ala Pro Ser Arg Asp Pro His Tyr Gln Asp Pro
    1115                1120                1125
His Ser Thr Ala Val Gly Asn Pro Glu Tyr Leu Asn Thr Val Gln
    1130                1135                1140
Pro Thr Cys Val Asn Ser Thr Phe Asp Ser Pro Ala His Trp Ala
    1145                1150                1155
Gln Lys Gly Ser His Gln Ile Ser Leu Asp Asn Pro Asp Tyr Gln
    1160                1165                1170
Gln Asp Phe Phe Pro Lys Glu Ala Lys Pro Asn Gly Ile Phe Lys
    1175                1180                1185
Gly Ser Thr Ala Glu Asn Ala Glu Tyr Leu Arg Val Ala Pro Gln
    1190                1195                1200
Ser Ser Glu Phe Ile Gly Ala
    1205                1210

<210> SEQ ID NO 5
<211> LENGTH: 20
<212> TYPE: DNA
<213> ORGANISM: Artificial Sequence
<220> FEATURE:

```
<223> OTHER INFORMATION: S100A9 S primer

<400> SEQUENCE: 5
cacccagaca ccctgaacca                                               20

<210> SEQ ID NO 6
<211> LENGTH: 20
<212> TYPE: DNA
<213> ORGANISM: Artificial Sequence
<220> FEATURE:
<223> OTHER INFORMATION: S100A9 AS primer

<400> SEQUENCE: 6
cctcgaagct cagctgcttg                                               20

<210> SEQ ID NO 7
<211> LENGTH: 20
<212> TYPE: DNA
<213> ORGANISM: Artificial Sequence
<220> FEATURE:
<223> OTHER INFORMATION: S100A8 S primer

<400> SEQUENCE: 7
atttccatgc cgtctacagg                                               20

<210> SEQ ID NO 8
<211> LENGTH: 20
<212> TYPE: DNA
<213> ORGANISM: Artificial Sequence
<220> FEATURE:
<223> OTHER INFORMATION: S100A8 AS primer

<400> SEQUENCE: 8
tgccacgccc atctttatca                                               20

<210> SEQ ID NO 9
<211> LENGTH: 20
<212> TYPE: DNA
<213> ORGANISM: Artificial Sequence
<220> FEATURE:
<223> OTHER INFORMATION: EGFR S primer

<400> SEQUENCE: 9
tccagtggcg ggacatagtc                                               20

<210> SEQ ID NO 10
<211> LENGTH: 20
<212> TYPE: DNA
<213> ORGANISM: Artificial Sequence
<220> FEATURE:
<223> OTHER INFORMATION: EGFR AS primer

<400> SEQUENCE: 10
agtcactggg ggacttgcca                                               20

<210> SEQ ID NO 11
<211> LENGTH: 20
<212> TYPE: DNA
<213> ORGANISM: Artificial Sequence
<220> FEATURE:
<223> OTHER INFORMATION: IL-1B S primer

<400> SEQUENCE: 11
tgagctcgcc agtgaaatga                                               20
```

```
<210> SEQ ID NO 12
<211> LENGTH: 20
<212> TYPE: DNA
<213> ORGANISM: Artificial Sequence
<220> FEATURE:
<223> OTHER INFORMATION: IL-1B AS primer

<400> SEQUENCE: 12
aagcccttgc tgtagtggtg                                          20
```

METHOD FOR TREATING MUSCLE-INVASIVE BLADDER CANCER, CONTAINING S100A9 AND EGFR INHIBITORS AND CISPLATIN AS ACTIVE INGREDIENTS

TECHNICAL FIELD

The present invention relates to a method for predicting the probability of recurrence or metastasis of muscle invasive bladder cancer (MIBC), a method for providing information about personalized medicine for MIBC, and a pharmaceutical composition for treatment of MIBC comprising inhibitors of S100A9 and EGFR and cisplatin as effective components.

BACKGROUND ART

Bladder cancer is the second most common genitourinary tumor, and more than 90% of these tumors are urothelial carcinomas. Almost 25% of patients with newly diagnosed bladder cancer have MIBC, with the vast majority of these tumors being of high histological grade. Moreover, nearly 50% of patients with MIBC already have occult distant metastases at the time of diagnosis.

Although radical cystectomy is the standard treatment for MIBC, about 50% of these patients develop metastases within 2 years, and the 5 year survival rate after surgery alone is approximately 50%. Systemic cisplatin-based combination chemotherapy is the first-line treatment modality for patients with metastatic bladder cancer. However, despite the initial high response rates of 40 to 70% reported in patients with advanced disease, chemotherapy is usually not curative and the overall 5 year survival is only 5 to 15%. Performance status and the presence of visceral metastases are well-established prognostic markers demonstrated to predict a poor prognosis in patients treated with cisplatin-based chemotherapy. However, while these clinicopathological markers are useful as survival indicators, they are inadequate to predict either the response rate or the survival rate in an individual patient. Accordingly, there is growing interest in the role played by genes in the chemotherapeutic response of patients with MIBC and the predictive power of this relationship in an individual patient.

Thus far, information that would allow the response to chemotherapy to be predicted in an individual patient is lacking in the case of MIBC as well as many other cancers. Consequently, some patients suffer the adverse side effects of these highly toxic drugs without the benefit of their intended action. Perhaps even more important is that, as their physical condition worsens, some of these unnecessarily treated patients may be deprived of additional therapy.

In our previous study, a gene expression profile analysis was carried out with the aim of identifying a genetic signature for progression in MIBC patients. Among the 1,320 genes thus identified by microarray data analysis, four genes (IL1B, S100A8, S100A9, and EGFR) were determined to be important in predicting disease progression. In the present study, we asked whether this four-gene signature could be used to predict disease progression after chemotherapy in patients with locally recurrent or metastatic MIBC.

PRIOR ART DOCUMENT

Patent Document

Patent Document KR 10-2007-0018108

DISCLOSURE

Technical Problem

The present invention is directed to providing a method for predicting the probability of recurrence or metastasis of MIBC.

Also, the present invention is directed to providing a method for providing information about personalized medicine for MIBC.

Further, the present invention is directed to providing a pharmaceutical composition for treatment of MIBC comprising inhibitors of S100A9 and EGFR and cisplatin as effective components.

Technical Solution

One aspect of the present invention provides a method for predicting the probability of recurrence or metastasis of MIBC by measuring expression levels of S100A9 and EGFR after chemotherapy.

Preferably, the expression levels may be mRNA or protein expression levels.

Another aspect of the present invention provides a method for providing information about personalized medicine for chemotherapy by measuring expression levels of S100A9 and EGFR from a patient with MIBC.

Preferably, the expression levels may be mRNA or protein expression levels.

Preferably, the chemotherapy may be cisplatin-based chemotherapy.

Further, still another aspect of the present invention provides a pharmaceutical composition for treatment of MIBC comprising inhibitors of S100A9 and EGFR and cisplatin as effective components.

Preferably, the inhibitors may be siRNAs of S100A9 and EGFR.

Preferably, the inhibitors may be protein inhibitors of S100A9 and EGFR.

Advantageous Effects

According to the present invention, it is possible to accurately predict the prognosis of a patient with MIBC after chemotherapy, and also possible to provide information about the sensitivity to cisplatin when providing personalized medicine for chemotherapy of a patient with MIBC, and still also possible to enhance the sensitivity of a patient with MIBC to cisplatin by a co-administration of inhibitors of S100A9 and EGFR together with an administration of cisplatin.

DESCRIPTION OF DRAWINGS

FIG. 5a to FIG. 5d show that EGFR expression coincides with apoptosis by cisplatin treatment.

MODES OF THE INVENTION

Figure 1:
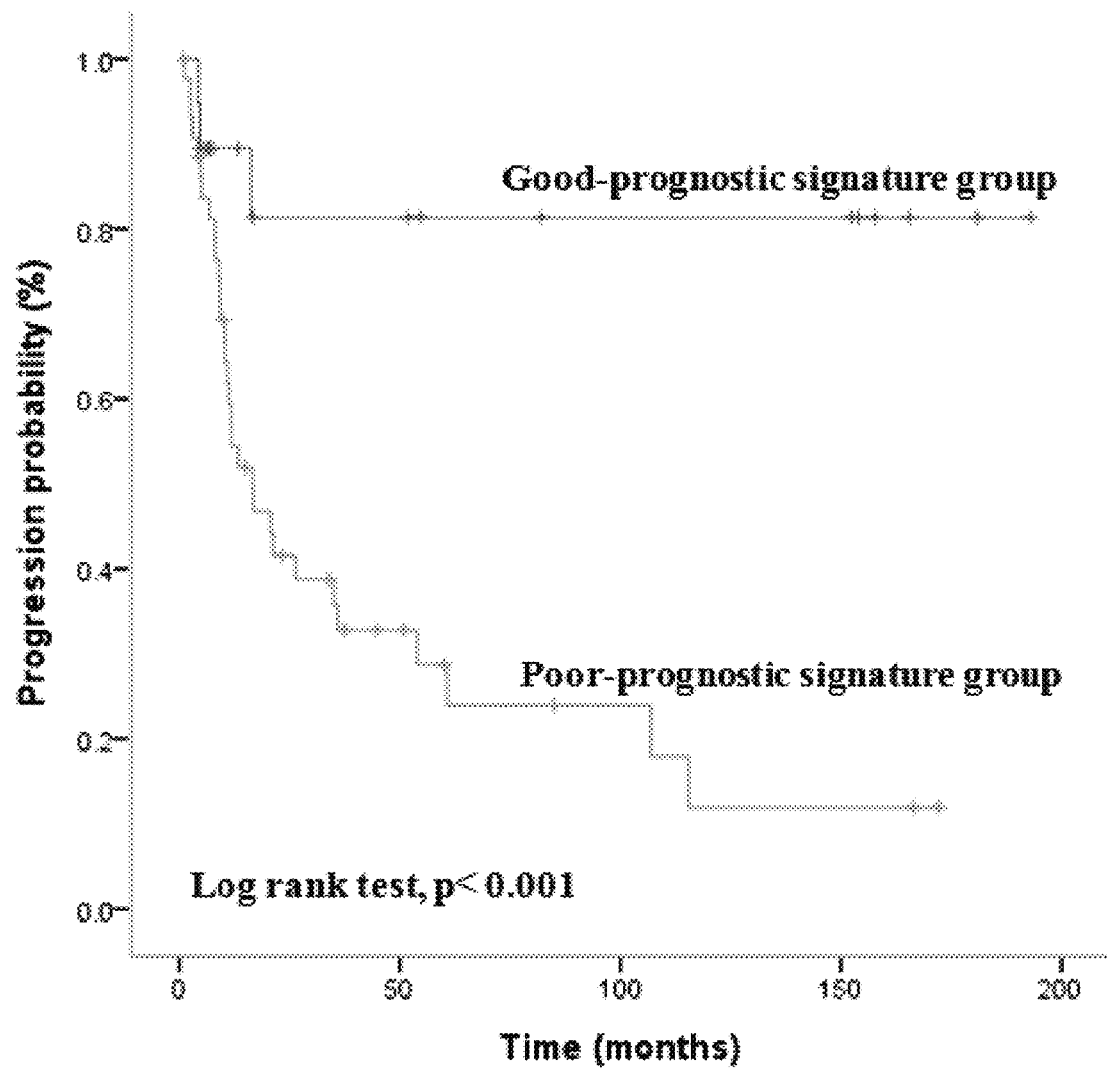
FIG. 1 is a graph that compares the progression probability over time in patients with recurrent or metastatic MIBC who received chemotherapy for each signature group.

Hereinafter, the present invention will be described in detail.

The present invention provides a method for predicting the probability of recurrence or metastasis of MIBC by measuring expression levels of S100A9 and EGFR after chemotherapy.

The inventors of the present invention confirmed that the probability of local recurrence or metastasis in a patient with MIBC after chemotherapy is correlated to the expression levels of S100A9 and EGFR.

To be more specific, most of the patients showing recurrence or metastasis of MIBC also show an increase in expression levels of S100A9 and EGFR. This means an increase in mRNA or protein expression levels of S100A9 and EGFR.

Further, the present invention provides a method for providing information about personalized medicine for chemotherapy by measuring expression levels of S100A9 and EGFR from a patient with MIBC.

The expression levels are mRNA or protein expression levels of S100A9 and EGFR, and the chemotherapy is cisplatin-based chemotherapy.

According to the above-described method of the present invention, it is possible to provide information about personalized medicine for cisplatin-based chemotherapy of a patient with MIBC.

Furthermore, the present invention provides a pharmaceutical composition for treatment of MIBC comprising inhibitors of S100A9 and EGFR and cisplatin.

Preferably, the inhibitors may be siRNAs or protein inhibitors of S100A9 and EGFR.

The pharmaceutical composition of the present invention remarkably enhances the chemo-sensitivity to cisplatin as compared with chemotherapy such as an administration of cisplatin alone. Thus, an administration of a small dose of medicine can achieve a result equivalent or superior to that of the administration of cisplatin alone.

The term "treatment", as used herein, unless otherwise indicated, means reversing, palliating, inhibiting the progress of, or preventing the disorder or disease to which such term applies, or one or more symptoms of the disorder or disease. The term "treatment", as used herein, refers to the act of treating as the term "treating" is defined above. Therefore, the "treatment" or "therapy" of a mammal with MIBC may include at least one of the following:

(1) Inhibiting the growth, i.e. development, of MIBC;
(2) Preventing proliferation, i.e. metastasis of MIBC;
(3) Relieving MIBC;
(4) Preventing recurrence of MIBC; and
(5) Palliating symptoms of MIBC.

Further, the composition for prevention or treatment of MIBC according to the present invention may comprise only the above-described effective components in pharmaceutically effective amounts or may comprise one or more pharmaceutically acceptable carriers, excipients, or diluents. The pharmaceutically effective amount means an amount sufficient to prevent, improve, and treat symptoms of the MIBC.

Furthermore, according to the present invention, the pharmaceutically effective amount can be appropriately changed depending on a degree of symptoms of MIBC, an age of a patient, a weight of a patient, a health condition of a patient, a sex of a patient, an administering route, a period of treatment, and the like.

Also, the pharmaceutically acceptable composition means that it is physiologically acceptable and a side effect or the similar effect thereof, such as a gastroenteric trouble, and dizziness, is not caused typically when being administered to humans. Examples of the carrier, excipient, and diluents may include lactose, dextrose, sucrose, sorbitol, mannitol, xylitol, erythritol, maltitol, starch, *acacia* rubber, alginate, gelatin, calcium phosphate, calcium silicate, cellulose, methylcellulose, polyvinylpyrrolidone, water, methyl hydroxybenzoate, propyl hydroxybenzoate, talc, magnesium stearate, and minerals. Further, they may additionally include fillers, anticoagulants, lubricants, wetting agents, flavoring, emulsifying agents, preservatives, and the like.

Further, the composition of the present invention may be formulated by using a method publicly known in the art in order to provide rapid, continuous, or delayed release of an active component after being administered to mammals. A dosage form may be powder, granule, tablet, emulsion, syrup, aerosol, soft or hard gelatin capsule, a sterile injection solution, or a sterile powder.

Furthermore, the composition for prevention or treatment of MIBC according to the present invention can be administered in various ways for example, orally, percutaneously, subcutaneously, intravenously or intramuscularly. A dosage of the active component may be selected appropriately depending on various factors, such as an administering route, an age, a sex, and a weight of a patient, severity of a patient, and the like. Further, the composition for prevention or treatment of MIBC according to the present invention may be administered along with a compound publicly known as having an effect of preventing, improving, or treating symptoms of MIBC.

Hereinafter, the present invention will be described in more detail with reference to Examples. However, Examples are just preferable examples, but do not limit the scope of the present invention.

EXAMPLE

Patients and Tissue Samples

In the present Example, the population consisted of patients with locally recurrent or metastatic MIBC who received chemotherapy. To minimize bias due to selection or knowledge of previous results, the patient cohort of the present Example was not the same as the one enrolled in the previous study of the inventors of the present invention on MIBC. Patients with locally recurrent MIBC underwent prior radical cystectomy but subsequently developed local or lymph node recurrence. Patients with metastatic MIBC had metastases to visceral organs. Only patients with good performance status (PS) (ECOG 0 or 1) were enrolled, thus removing the confounding effect of this functional parameter. All of the enrolled patients had been treated with at least four cycles of the cisplatin-based chemotherapy. Patients additionally treated with radiation therapy for any reason or patients who had experienced serious complications associated with surgery were excluded. Regardless of radical cystectomy status, patients who had not undergone an imaging work-up, such as CT scan or MRI, at least once per 3 months were also excluded from the study. Primary MIBC samples were obtained at the institute, to which the inventors of the present invention belong, from the 69 patients with histologically verified urothelial carcinoma who were enrolled in the study of the present Example.

All tumors were macro-dissected, typically within 15 minutes of surgical resection. Each bladder cancer specimen was confirmed as representative by analysis of adjacent tissue in fresh frozen sections from cystectomy and transurethral resection specimens. The tumor specimens were then frozen in liquid nitrogen and stored at −80° C. until use. Both the collection and the analysis of all samples were approved by the Institutional Review Board of Chungbuk National University. Informed consent was obtained from each patient enrolled in the study of the present Example (IRB approval number: 2006-01-001).

Tumors were staged according to the 2002 TNM classification and the 1973 WHO grading system. In the present Example, disease progression was defined as newly diagnosed distant metastasis and a 20% increment in the MIBC tumor mass after chemotherapy.

Reagents

TRIzol and First-Strand cDNA synthesis kit were purchased from Invitrogen (Carlsbad, Calif.) and from Amersham Biosciences (Freiburg, Germany). Ventana Ultraview DAB Kit was purchased from Ventana Medical Systems (Tucson, Ariz.). Heat-inactivated fetal bovine serum (FBS) and Lipofectamine 2000 were purchased from Invitrogen. Protease inhibitor cocktail tablets were purchased from Roche Diagnostics (Basel, Switzerland). The Micro BCA protein assay kit was obtained from Pierce (Rockford, Ill.). Premade SDS-PAGE gels, Coomassie Blue R-250 staining solution and destaining solution were purchased from Bio-Rad (Hercules, Calif.). Small interfering RNAs (siRNAs) against EGFR, S100A9 and NON-TARGET controls were purchased from Dharmacon (Chicago, Ill.). Antibodies against EGFR and β-actin were purchased from Cell Signaling Technology (Danvers, Mass.). Antibody against S100A9 was purchased from AbCam (West Grove, Pa.). All other reagents were obtained from Sigma-Aldrich or Promega (Madison, Wis.).

RNA Extraction and cDNA Synthesis

Total RNA isolated from malignant bladder tissue using 1 ml of TRIzol was homogenized in a 5 ml glass tube. The homogenate was transferred to a 1.5 ml tube and then mixed with 200 μl of chloroform. After a 5-min incubation at 4° C., the homogenate was centrifuged for 13 minutes at 13,000×g and 4° C. The upper aqueous phase was transferred to a clean tube to which 500 μl of isopropanol was added. These samples were incubated for 60 minutes at 4° C. and centrifuged for 8 minutes at 13,000×g and 4° C. The upper aqueous phase was discarded and the pellet was resuspended with 500 μl of 75% ethanol, followed by a 5-min centrifugation at 13,000×g and 4° C. The upper aqueous layer was removed and the pellet was dried at room temperature, dissolved in diethylpyrocarbonate (DEPC)-treated water, and then stored at −80° C. The quality and integrity of the RNA were confirmed by agarose gel electrophoresis and ethidium bromide staining followed by visual inspection under ultraviolet light. The cDNA was prepared using 1 μg of random primers and a First-Strand cDNA synthesis kit (Amersham Biosciences Europe GmbH, Freiburg, Germany) according to the manufacturer's protocol.

RT-PCR Analysis

The expression of four genes was quantified by real-time PCR using a Rotor-Gene 6000 system (Corbett Research, Mortlake, Australia). The assays were carried out in micro-reaction tubes (Corbett Research, Mortlake, Australia) using SYBR Premix EX Taq (TAKARA BIO INC., Otsu, Japan).

The primers used to amplify the four genes analyzed in the present invention are shown in Table 1.

TABLE 1

| Gene | Primer |
|------|--------|
| S100A9 | S: 5'-CACCCAGACA CCCTGAACCA-3'<br>AS: 5'-CCTCGAAGCT CAGCTGCTTG-3' |
| S100A8 | S; 5'-ATTTCCATGC CGTCTACAGG-3'<br>AS: 5'-TGCCACGCCC ATCTTTATCA-3' |
| EGFR | S: 5'-TCCAGTGGCG GGACATAGTC-3'<br>AS: 5'-AGTCACTGGG GGACTTGCCA-3' |
| IL-1B | S: 5'-TGAGCTCGCC AGTGAAATGA-3'<br>AS: 5'-AAGCCCTTGC TGTAGTGGTG-3' |

S: sense, AS: antisense.

The PCR consisted of 5 μl of 2× SYBR Premix EX Taq buffer, 0.5 μl of each of the sense and antisense primers (10 pmol/μl), and 1 μl of the sample cDNA, in a final reaction volume of 10 μl. The amplified products were purified with a QIAquick extraction kit (QIAGEN, Hilden, Germany) and quantified with a spectrophotometer (Perkin Elmer MBA2000, Fremont, Calif.). Fragments were sequenced using an automated laser fluorescence sequencer (ABI PRISM 3100 Genetic Analyzer, Foster City, Wis.). Ten-fold serial dilutions were prepared to obtain known concentrations of product in the range of 100 to 0.1 pg/μl. This dilution series was then used to establish a standard curve for real-time PCR, carried out under the following conditions: (i) denaturation, 1 cycle of 20 seconds at 96° C. followed by 40 cycles of 2 seconds at 96° C.; (ii) annealing, 15 seconds at 60° C.; and (iii) extension, 15 seconds at 72° C. The melting program was performed within a temperature range of 72 to 95° C., with heating at a rate of 1° C. per 45 seconds. Spectral data were captured and analyzed using Rotor-Gene Real-Time Analysis Software 6.0 Build 14 (Corbett Research, Mortlake, Australia). All samples were run in triplicate. Gene expression was normalized to β-globin expression.

Immunohistochemical Staining

Paraffin blocks from 38 bladder cancer cases were used for immunohistochemical analysis. Tissue sections were cut and placed on Superfrost Plus microscope slides (Fisher Scientific). Using the Benchmark XT automated immunohistochemistry stainer (Ventana Medical Systems, Inc., Tucson, Ariz., USA), slides were stained by the following procedure. Detection was done using the Ventana Ultraview DAB Kit (Ventana Medical Systems). Sections were deparaffinized using EZ Prep solution. CC1 standard (pH 8.4 buffer containing Tris/Borate/EDTA) was used for antigen retrieval. DAB inhibitor (3% $H_2O_2$, Endogenous peroxidase) was blocked for 4 minutes at 37° C. Sections were incubated with an anti-EGFR (Abcam Inc., San Diego, Calif., dilution 1/100) and anti-S100A9 primary antibody (Abcam Inc., San Diego, Calif., dilution 1/100) for 40 minutes at 37° C., and a secondary antibody of Univeral HRP Multimer for 8 minutes at 37° C. Slides were treated on a DAB+$H_2O_2$ substrate for 8 min followed by hematoxylin and bluing reagent counterstain at 37° C. Reaction buffer (pH 7.6 Tris buffer) was used as a washing solution. Staining intensity and proportion of positively-stained cells were evaluated. EGFR and S100A9 localized primarily to the cytoplasm. Staining intensity was classified as follows: none, weak, moderate and strong. Each specimen was examined and scored separately by three investigators, and discrepancies were discussed until agreement was reached.

Cell Culture and Transfection

T24 human bladder cancer cells were purchased from American Type Culture Collection (ATCC, Manassas, Va.) and maintained in RPMI1640 media (Invitrogen, Carlsbad, Calif.) with 10% FBS and 1% Penicillin/Streptomycin at 37° C. under 5% $CO_2$. T24 cells at ~80% confluence were transiently transfected with expressing constructs or small interfering RNAs (siRNAs) of EGFR and S100A9 using Lipofactamine 2000. For S100A9 overexpression, pCMV-Sports6-S100A9 and vector constructs were kindly provided by Dr. A. Moon (Duksung University, Korea). As transfection controls, empty (Ctrl) or NON-TARGET control siRNAs (siCtrl) were used.

Western Blot Analysis

Whole cell lysates were extracted with NP40-containing lysis buffer (1% Nonidet P-40, 50 mM Tris pH 7.4, 10 mM NaCl, 1 mM NaF, 5 mM $MgCl_2$, 0.1 mM EDTA, 1 mM PMSF, and protease inhibitor cocktail) on ice. After vigorous vortexing, lysates were centrifuged at 12,000×g for 15 minutes to remove debris. Protein concentration was determined by microBCA (Pierce/Thermo Scientific) and 25 µg of proteins were subjected to SDS-PAGE separation and following western blot analysis. Secondary antibodies and the Micro BCA protein assay kit were obtained from Pierce (Rockford, Ill., USA). The ECL™ detection system was used for blotting signal detection, which was followed by densitometry (Amersham Biosciences, Little Chalfont, UK) to measure band intensities.

Wound-Healing Assay

Wound healing assays were performed in 6-well plates after cell density reached to about 90%. Gentle scratch on T24 cells was done with a sharp tip, and the plates were incubated for additional 8 hours before observation under microscope.

Cell Proliferation Assay

T24 bladder cancer cells were plated onto 6-well culture plates at a density of $5 \times 10^3$ cells per well in 10% FBS-containing growth medium. To overexpress S100A9, transient transfection was performed using Lipofectamine 2000. 24 hours after transfection, cells were serum-starved for 16 hours. Medium was replaced with normal growth medium for proliferation assay. A cell proliferation rate was determined by crystal violet staining at 0, 1 and 2 days. Briefly, cells were stained with a crystal violet solution and quantified by dissolving the stained cells in a 10% acetic acid solution. Colorimetric measurement was done by reading absorbances at 570 nm.

Cell Viability Assay

T24 cells were transfected with various constructs or siRNAs, and the cells were incubated with drugs (e.g. cisplatin or Iressa) containing serum free medium for the indicated time. Cell viability was determined using MTS reagents as instructed by the manufacturer's protocol (Promega Corporation, Madison, Wis.).

Data and Statistical Analysis

Due to the highly skewed distribution of the mRNA expression levels of each gene, the data were natural-log-transformed and then back-transformed for the interpretation of the results. The association between disease progression after chemotherapy and the gene signatures was evaluated using univariate Cox regression analysis. Time to progression was calculated according to the Kaplan-Meier method, with differences between the times assessed using log-rank statistics.

After univariate Cox analysis of the four progression-related genes, two were used to calculate a risk score of disease progression for each patient, defined as the sum of the levels of expression of each gene multiplied by the corresponding regression coefficient. ROC curves identified the optimal cutoff point of each risk score that yielded the highest combined sensitivity and specificity for disease progression. Based on these values, the patients were classified into either the good- or the poor-prognostic gene signature group. The prognostic value of the gene expression signature was determined by multivariate Cox proportional hazard regression models. The association between disease progression after chemotherapy and results of the immunohistochemical staining was evaluated using Fisher's exact test, and the correlation between the mRNA expression level and the immunohistochemical staining intensity was evaluated by Spearman rank correlation. In in vitro experiments, p-values were calculated using unpaired Student's t-test. Statistical analysis was performed using SPSS 19.0 software (SPSS Inc., Chicago, Ill.), with $p<0.05$ considered statistically significant.

Results

Baseline Characteristics

The mean age of the 69 patients who received chemotherapy was 64.74±8.97 years, and the mean follow-up period was 46.24±56.24 months. 54 (78.3%) patients had local recurrence without visceral metastasis and 15 (21.7%) patients had metastases to other organs. 40 (58.0%) patients underwent prior radical cystectomy. Other baseline characteristics of the patients are presented in Table 2.

TABLE 2

| Variables | Incidence or mean value (%) |
|---|---|
| Age (years) | 64.74 ± 8.97 |
| Median follow-up (months) | 46.24 ± 56.24 |
| Gender | |
| Male | 57 (82.6) |
| Female | 12 (17.4) |
| Grade | |
| 2 | 25 (36.2) |
| 3 | 44 (63.8) |
| Stage | |
| Advanced (any T, N1 or N2, and M0) | 54 (78.3) |
| Metastasis (any T, any N, and M1) | 15 (21.7) |
| Prior radical cystectomy | |
| No | 29 (42.0) |
| Yes | 40 (58.0) |

Identification of Genes Associated with Disease Progression in Locally Recurrent or Metastatic MIBC Univariate Cox regression analysis of four genes (IL1B, S100A8, S100A9, and EGFR), which were previously determined to play an important role in MIBC progression, was performed. Two of them, S100A9 and EGFR, significantly correlated to disease progression (p=0.023, p=0.045, respectively). These two genes were then used to calculate a risk score of disease progression after chemotherapy in MIBC patients. The risk score identified two groups of patients. A good-prognostic signature group represented relatively low expression levels of the two genes, while a poor-prognostic signature group had significantly higher expression. A cutoff value (36.1683) was determined for disease progression with the highest combined sensitivity (91.9%) and specificity (56.3%) based on the ROC curve.

Prognostic Value of the Two-Gene Signature for Disease Progression in Patients with Locally Recurrent or Metastatic MIBC A comparison of the two groups showed that the time to progression was significantly longer in the good-prognostic signature group (p<0.001) (FIG. 1). Univariate Cox regression analysis showed that metastasis, prior cystectomy, and combined gene signature were significant influential factors for disease progression after chemotherapy (Table 3). In multivariate Cox regression analysis, only combined gene signature was a significant influential factor for disease progression in patients with locally recurrent or metastatic MIBC after chemotherapy (Table 3).

TABLE 3

| | Disease progression after chemotherapy | | | |
|---|---|---|---|---|
| | Univariate Cox regression | | Multivariate Cox regression | |
| Variables | HR (95% CI) | p-values | HR (95% CI) | p-values |
| Age (years) | 1.006 (0.969-1.045) | 0.743 | 0.998 (0.962-1.036) | 0.922 |
| Gender (male vs female) | 0.597 (0.272-1.313) | 0.200 | 0.780 (0.342-1.776) | 0.554 |
| Grade (grade2 vs grade3) | 0.955 (0.484-1.884) | 0.894 | 1.462 (0.649-3.293) | 0.360 |
| Stage (advanced vs metastatic) | 2.762 (1.332-5.771) | 0.007 | 2.157 (0.948-4.906) | 0.067 |
| Prior radical cystectomy (no vs yes) | 0.378 (0.190-0.751) | 0.005 | 0.533 (0.233-1.217) | 0.135 |
| combined gene signature (good vs poor) | 6.862 (2.088-22.553) | 0.002 | 5.380 (1.570-18.436) | 0.007 |

Figure 2A:
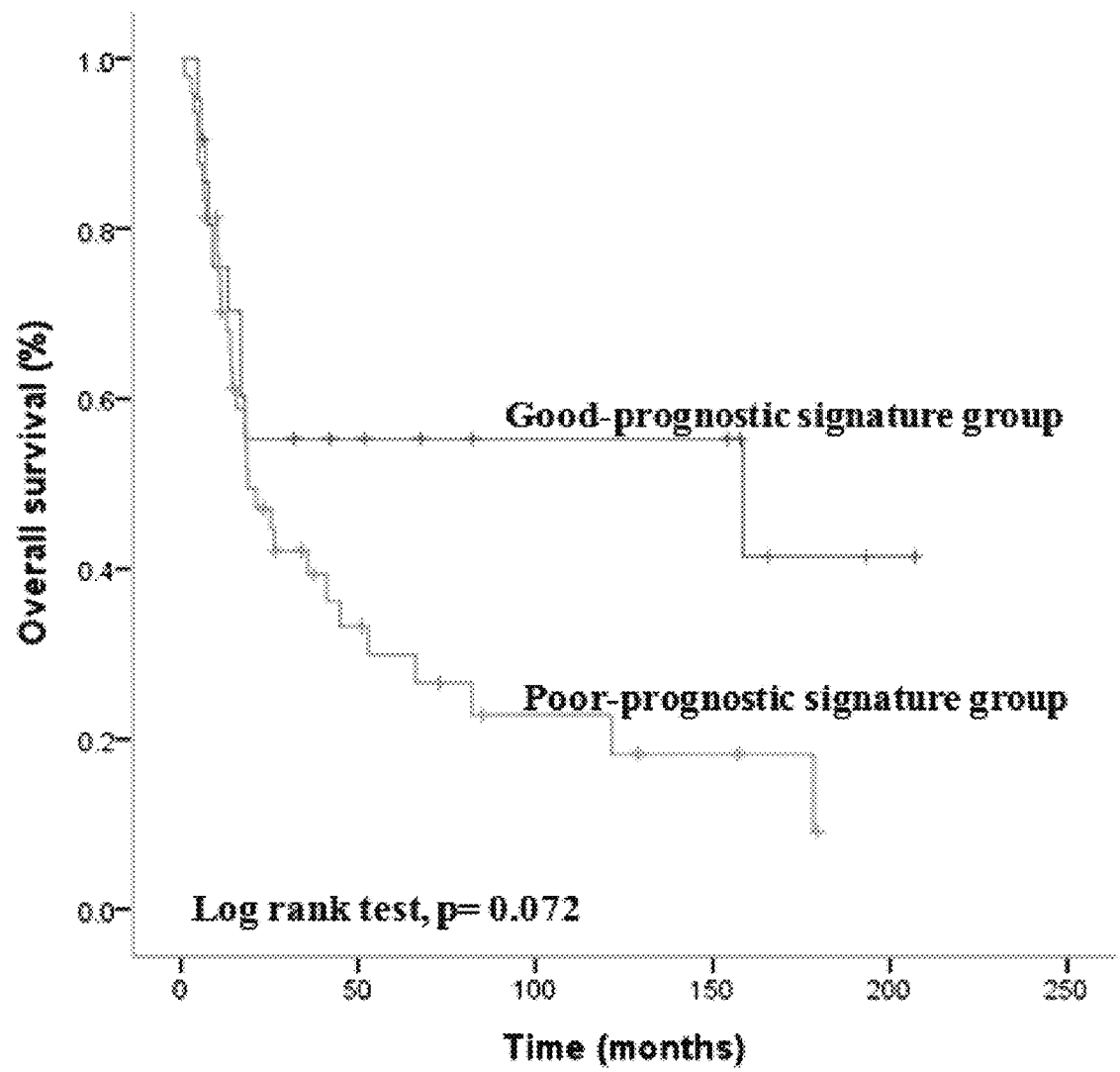
FIG. 2a and FIG. 2b are graphs that compare the overall survival and cancer-specific survival over time in patients with recurrent or metastatic MIBC who received chemotherapy for each signature group.
Figure 2B:
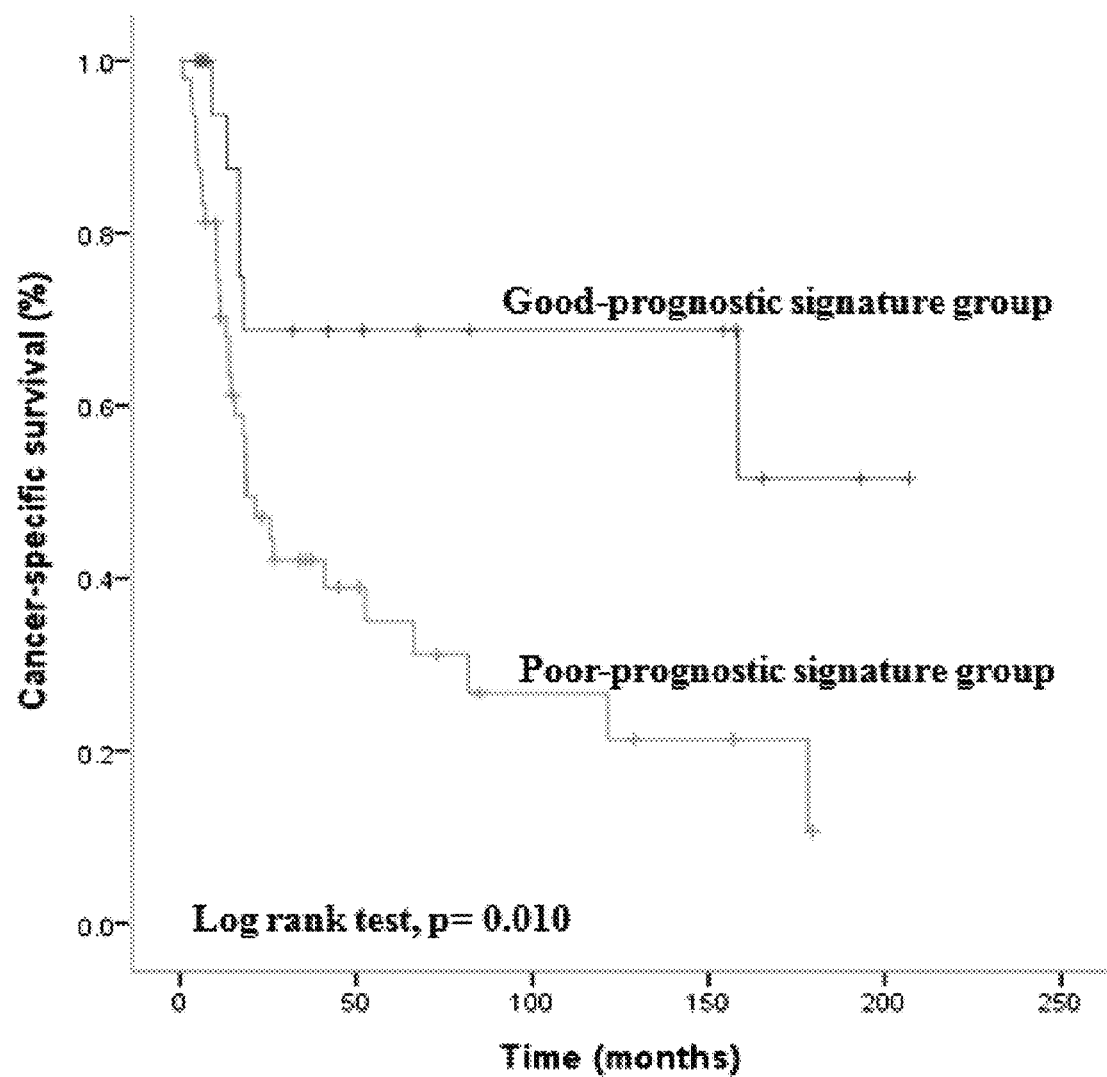

The good-prognostic signature group had a significantly longer cancer-specific survival time than the poor-prognostic signature group (p=0.010) (FIG. 2b). However, the overall survival time was only marginally enhanced in the good-prognostic signature group (p=0.072) (FIG. 2a).

Immunohistochemical Staining of S100A9 and EGFR in Bladder Cancer

Figure 3A:
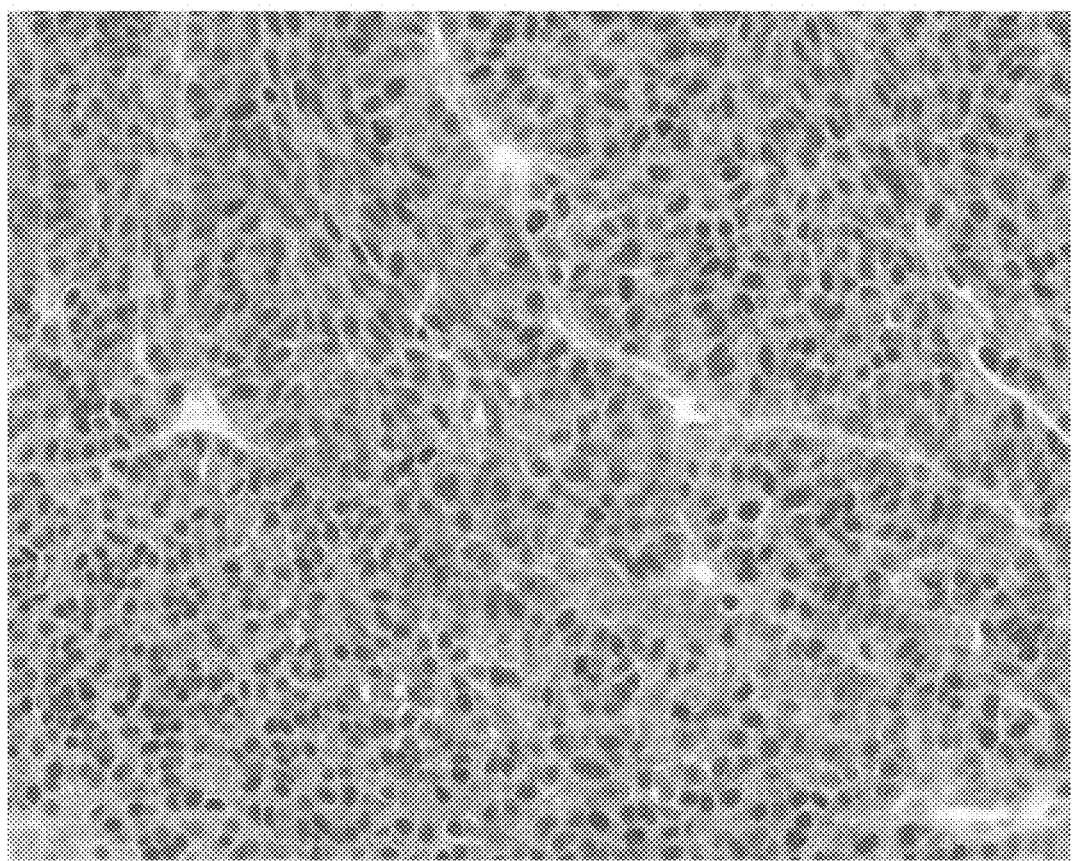
FIG. 3a to FIG. 3f are respectively images and graphs showing immunohistochemical staining for S100A9 and EGFR in bladder cancer.
Figure 3B:
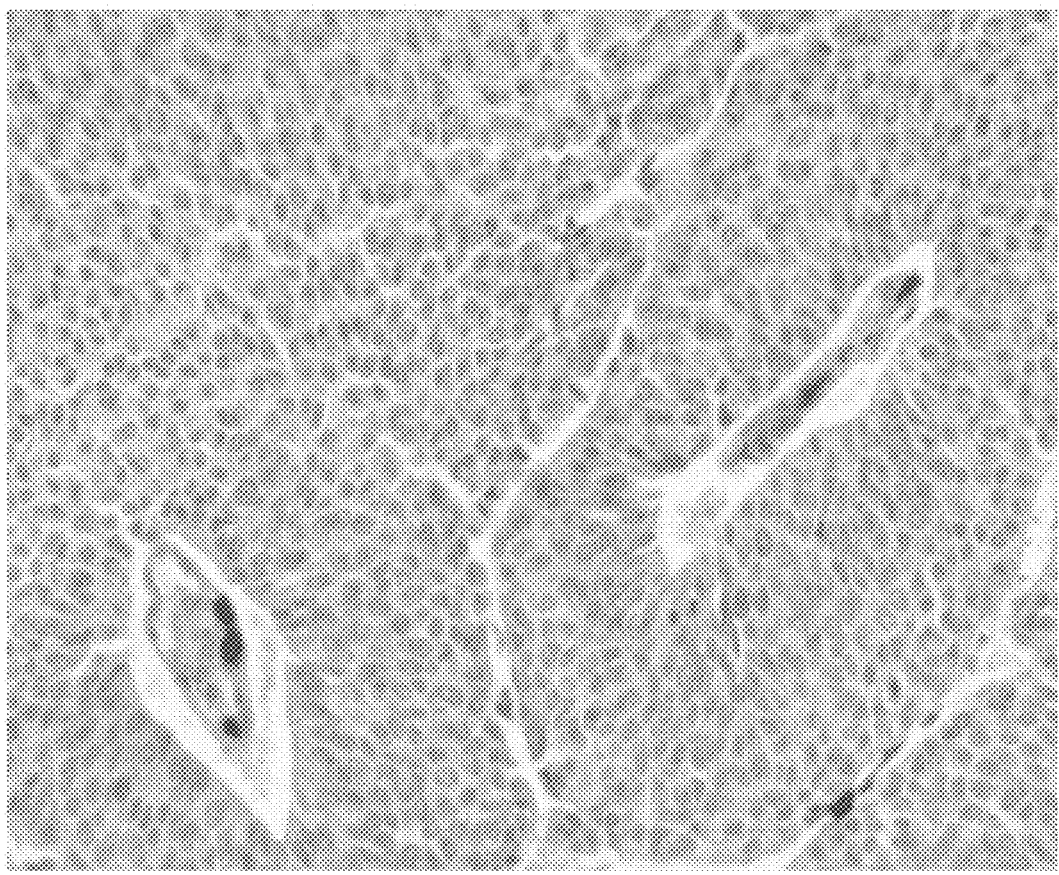
Figure 3C:
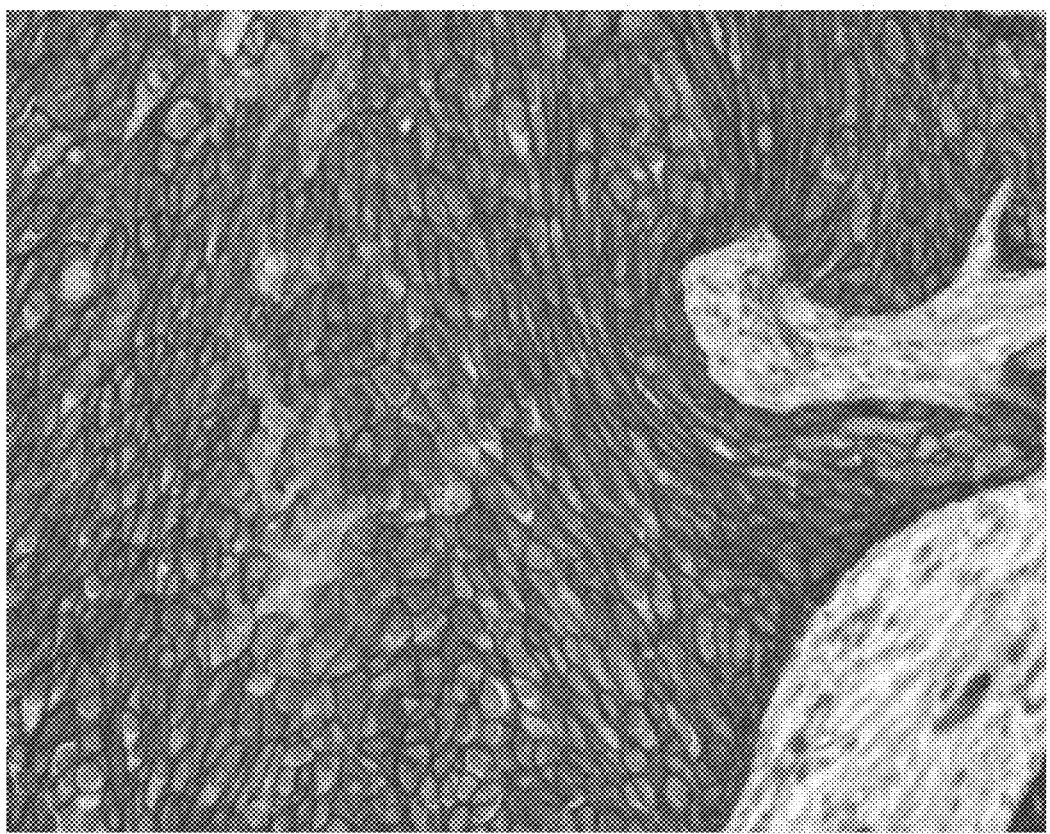
Figure 3D:
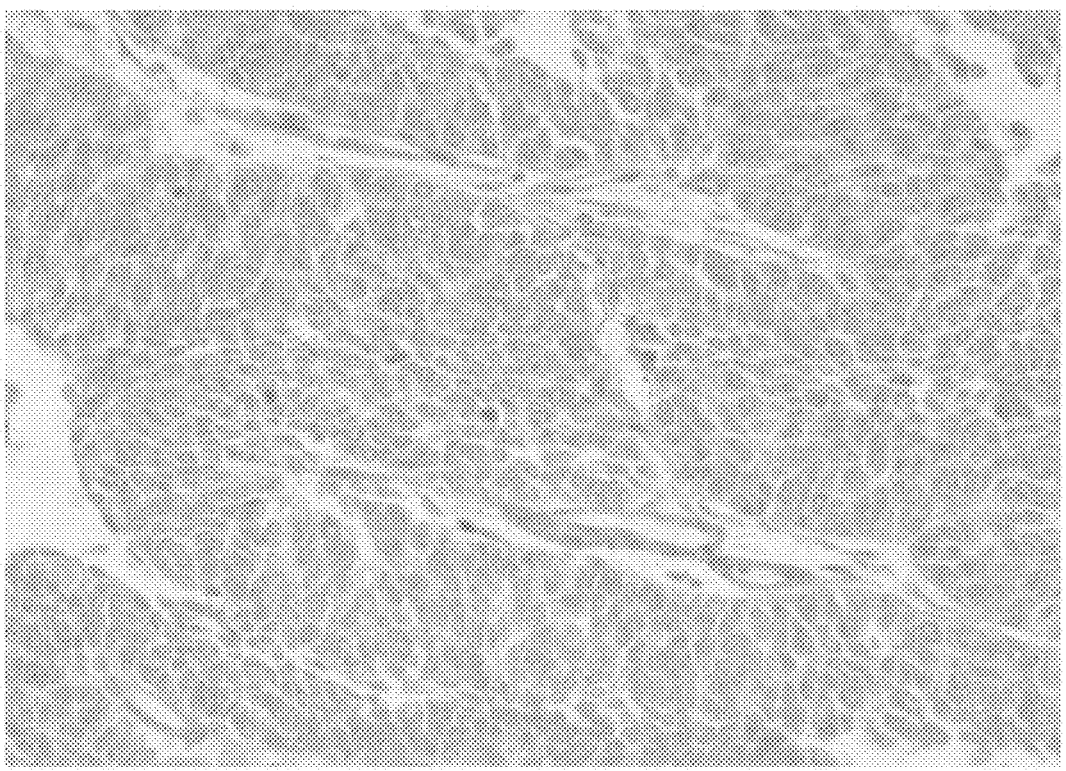
Figure 3E:
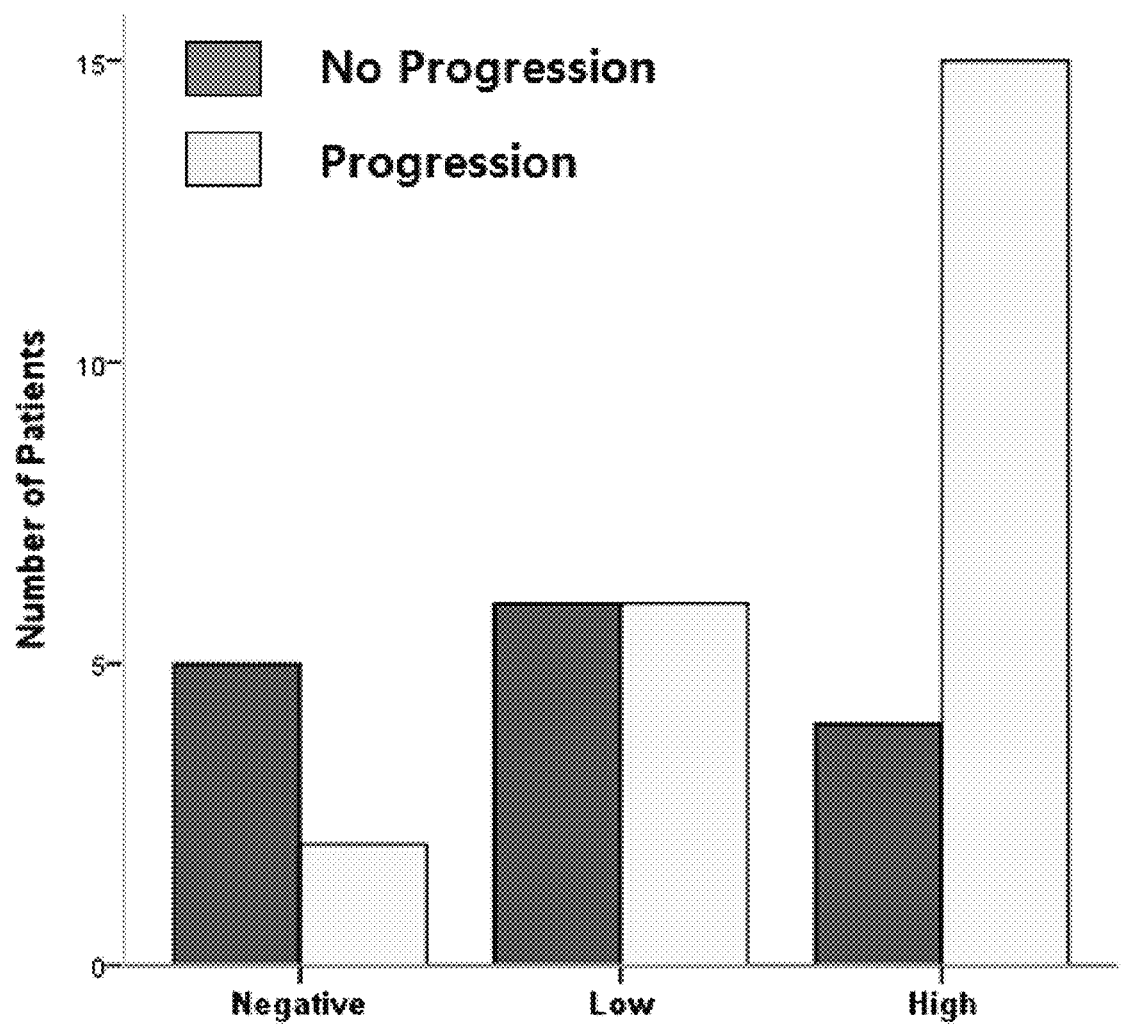
Figure 3F:
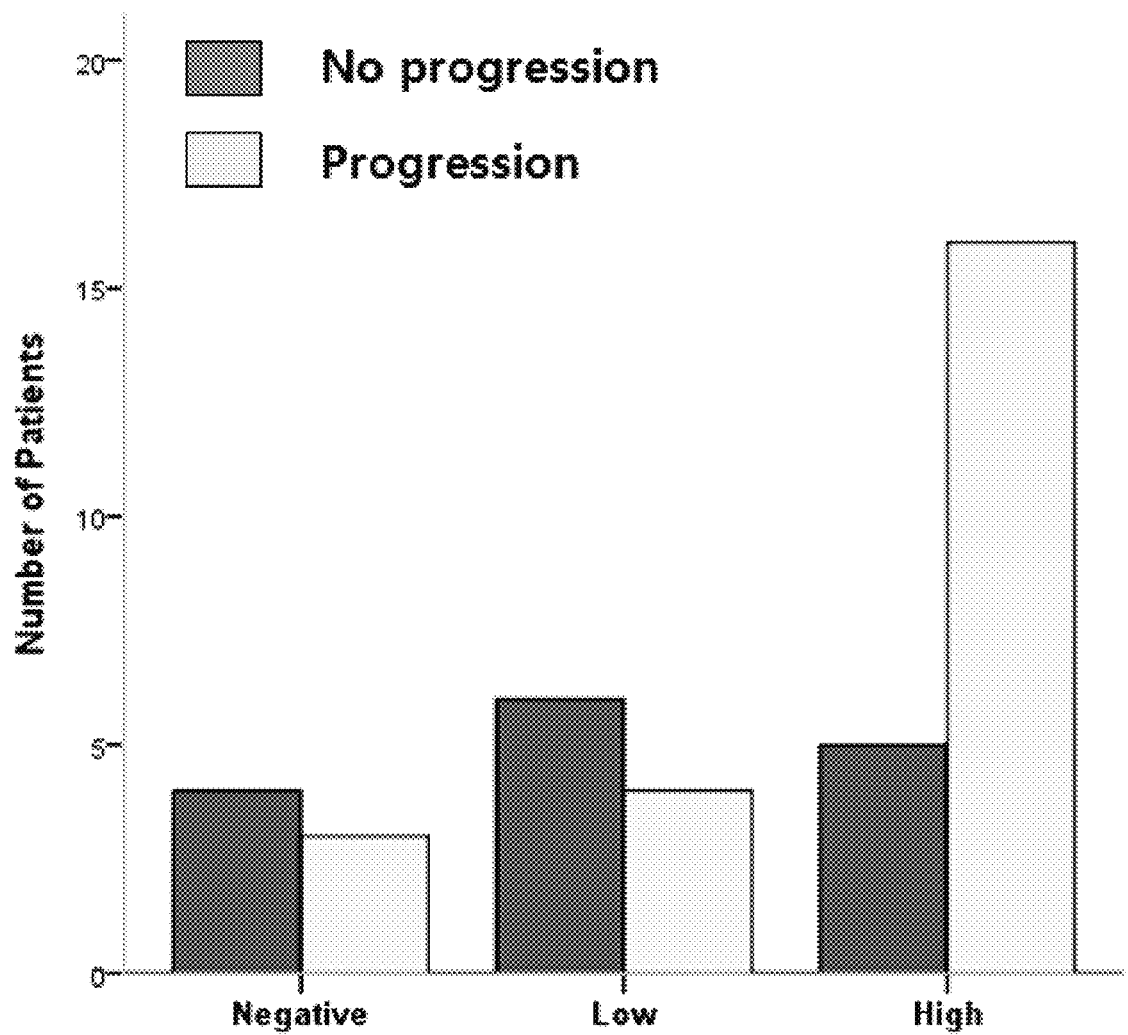
Figure 4A:
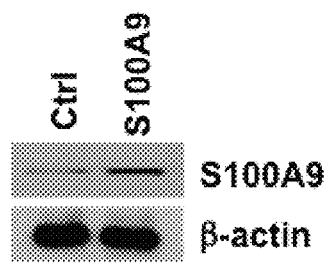
FIG. 4a to FIG. 4d show that overexpressed S100A9 leads to the enhanced migration, proliferation, and resistance to cisplatin-induced cell apoptosis.
Figure 4B:
Figure 4C:
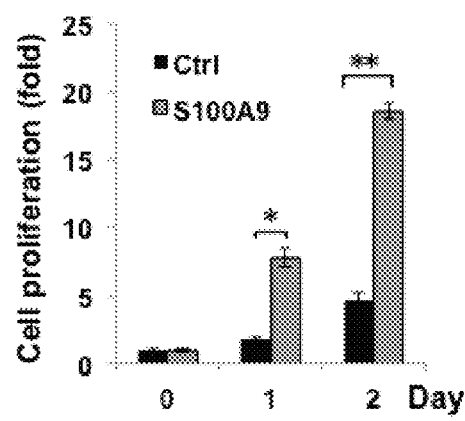
Figure 4D:
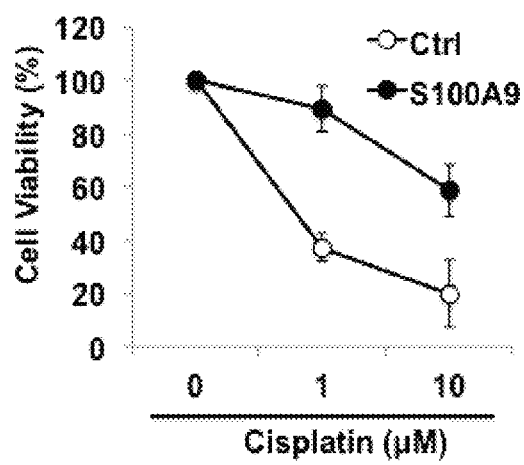

To expand the present inventors' findings suggesting that S100A9/EGFR may be a novel diagnostic marker for MIBC with local recurrence or metastasis after chemotherapy, the inventors of the present invention assessed the value of S100A9/EGFR protein as a prediction marker. The protein expression levels of the S100A9 and EGFR protein were assessed in 38 bladder cancer samples by immunohistochemical analysis. Various intensities (from negative to strong) of S100A9 and EGFR were observed in cancer tissues (FIG. 3a to FIG. 3f). S100A9 were detected in cytoplasm as well as nucleus (FIG. 3a), while EGFR was detected in cytoplasm, nucleus and plasma membrane (FIG. 3c). EGFR positivity was marginally associated with disease progression after chemotherapy in our MIBC patients (p=0.106). However, S100A9 positivity was strongly correlated to disease progression (p=0.047). 65% (15 among 23) of bladder cancer patients with progression after chemotherapy exhibited high S100A9 levels, while only 26% (4 among 15) of patients without progression showed high intensities (Table 4). Furthermore, the combined approach of S100A9 and EGFR were much significantly associated with progression (p=0.018). 73.9% (17 among 23) patients with progression showed high S100A9/EGFR staining, and no patient has negative staining of S100A9/EGFR (Table 4). Notably, we found that protein expression intensities of S100A9 and EGFR showed good correlation with mRNA levels of S100A9 and EGFR (r=0.395, p=0.014 and r=0.453, p=0.004).

TABLE 4

| | Disease progression (+) after chemotherapy N = 23 (%) | Disease progression (−) after chemotherapy N = 15 (%) | p-value |
|---|---|---|---|
| EGFR staining | | | 0.106 |
| High | 16 (76.2) | 5 (23.8) | |
| Low | 4 (33.3) | 6 (66.7) | |
| Negative | 3 (42.9) | 4 (57.1) | |
| S100A9 staining | | | 0.047 |
| High | 15 (78.9) | 4 (21.1) | |
| Low | 6 (50.0) | 6 (50.0) | |

TABLE 4-continued

| | Disease progression (+) after chemotherapy N = 23 (%) | Disease progression (−) after chemotherapy N = 15 (%) | p-value |
|---|---|---|---|
| Negative | 2 (28.6) | 5 (71.4) | |
| Combined (EGFR + S100A9) | | | 0.018 |
| High[†] | 17 (77.3) | 5 (22.7) | |
| Intermediate[‡] | 6 (42.9) | 8 (57.1) | |
| Negative | 0 (0) | 2 (100) | |

High[†]: high + high and high + low
Intermediate[‡]: high + negative, low + low and low + negative Hyper-Proliferation Caused by S100A9 Overexpression and Cisplatin-Induced Apoptosis Two independent expression analyses (based on qRT-PCR and IHC) performed by the inventors of the present invention suggest S100A9/EGFR as a novel prognostic marker in bladder cancer for disease progression after cisplatin-based chemotherapy. To assess the hypothesis that S100A9 and EGFR have important function in chemo-resistance, we have attempted in vitro functional analysis to test whether the altered gene expression of S100A9 or EGFR regulates chemo-sensitivity to cisplatin treatment. Data from previous papers from the inventors of the present invention and other laboratories suggested that S100A9 may play an essential role during bladder cancer progression. Recent proteomics analysis revealed that a protein level of S100A9 is correlated to bladder tumor grade (p<0.05). S100A9 was also reported by the inventors of the present invention as one of four-gene signature of diagnostic markers in MIBC. To uncover whether S100A9 has a functional link to chemo-sensitivity of bladder cancer and to test this hypothesis in vitro, T24 cells were transfected with S100A9 overexpressing construct or control, and it was found that S100A9 involves in migration and proliferation of bladder cancer cells (B and C of FIG. 4). As shown in B of FIG. 4, the wound-healing assay revealed that transfected bladder tumor cells with S100A9 construct moved faster and filled the path earlier than control cells. Enforced S100A9 significantly enhanced proliferation rate of T24 cells in growth medium, compared to control cells (Ctrl, transfected T24 cells with a vector only). The increased S100A9 level allowed T24 cells more viable in the presence of cisplatin. Cell viability of control cells was reduced to about 20% after 2 days treatment with 10 μM cisplatin. In contrast, S100A9 expressing cells showed about 60% of viable cells by same treatment (D of FIG. 4). Increased expression level of S100A9 was confirmed by western blot analysis (A of FIG. 4).

Change in Response to Cisplatin-Induced Apoptosis Depending on EGFR Expression Level The inventors of the present invention performed gain- and loss-of functional studies in T24 bladder cancer cells to assess the biological role of EGFR. Overexpression of EGFR enhanced cell viability in the presence of 10 μM cisplatin in serum free medium. Control T24 cells transfected with empty vector showed 50% viability after 18 h-cisplatin treatment, while EGFR overexpressing cells did not show significant apoptosis until 24 h-treatment (B of FIG. 5). Knockdown of EGFR using RNAi sensitizes T24 cells to cisplatin-induced apoptosis (D of FIG. 5). Control RNAi (siCtrl) showed about 80% of cell viability 6 hours after cisplatin treatment, while two sets of EGFR knockdown (siEGFR-1 and siEGFR-2) both displayed only 30 to 40% of viability of controls (D of FIG. 5). Protein levels after overexpression or knockdown of EGFR were confirmed by western blot analysis (A and C of FIG. 5).

Figure 6:
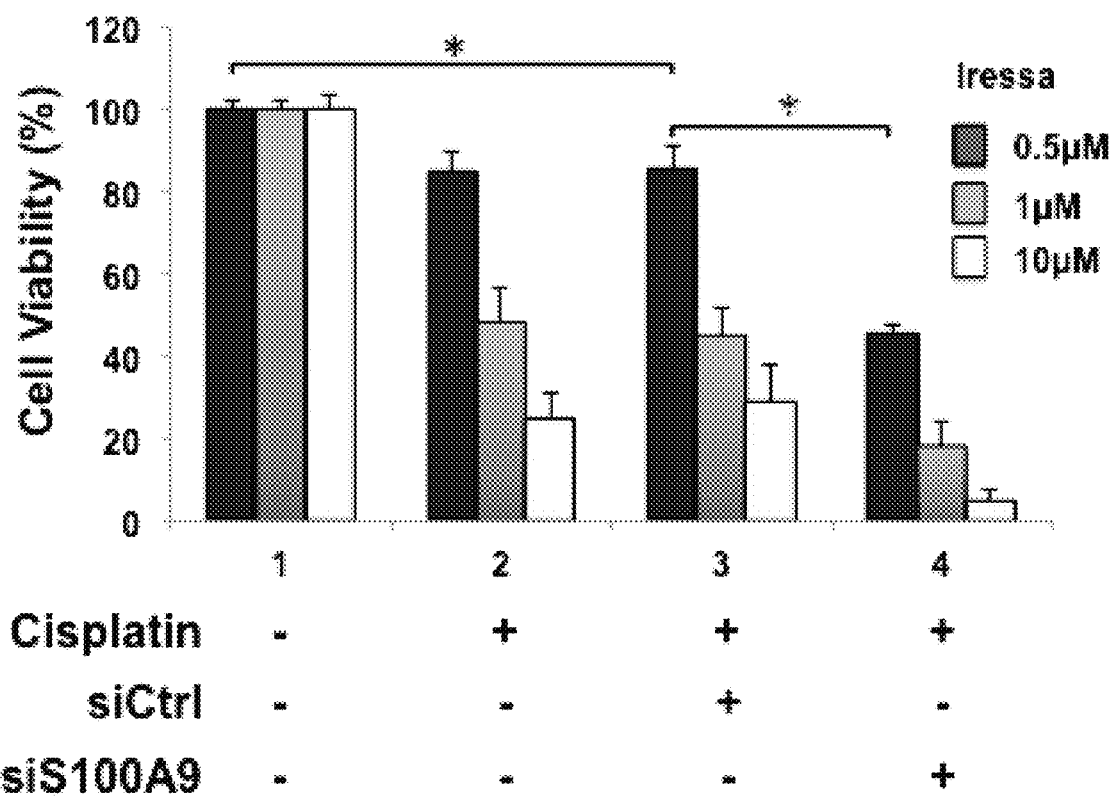
FIG. 6 shows that inhibition of S100A9 and EGFR leads to an increased sensitivity to cisplatin treatment.

Synergistic Effect on Sensitization of T24 Bladder Cancer Cells to Cisplatin-Induced Apoptosis Caused by Inhibition of Both S100A9 and EGFR Experimental data in FIG. 6 suggest that S100A9 and EGFR play roles in response to a chemotherapeutic reagent, cisplatin, in bladder cancer cells. The inventors of the present invention tested whether downregulation of EGFR and S100A9 alters levels of cisplatin-induced apoptosis. EGFR kinase activity was downregulated by Iressa (ZD1839, gefitinib), an EGFR kinase inhibitor. S100A9 was silenced using RNAi approach. Control siRNA was used for a control for non-target effect by siRNA. EGFR inhibition (with Iressa) significantly reduced viability, and enhanced chemo-sensitivity to cisplatin (FIG. 6, line 2). Moreover, combined inhibition of S100A9 and EGFR synergistically enhanced chemo-sensitivity of T24 bladder cancer cells (FIG. 6, line 4), suggesting the potential therapeutic strategy overcoming the chemo-resistance, which is often observed during cisplatin-based chemotherapy on bladder cancer patients.

While the present invention has been shown and described with reference to preferable Examples thereof, it will be understood by those skilled in the art that various changes in form and details may be made therein without departing from the spirit and scope of the present invention as defined by the appended claims. Therefore, the disclosed Examples should not be considered in view of explanation, but no limitation. The technical scope of the present invention is taught in the claims, but not the detailed description, and all the differences in the equivalent scope thereof should be construed as falling within the present invention.

The invention claimed is:

1. A method for treating muscle invasive bladder cancer (MIBC) comprising administering to a subject in need thereof a therapeutically effective amount of antibodies against S100A9 and EGFR, and cisplatin.

* * * * *